United States Patent
Tsuji et al.

(10) Patent No.: US 7,625,730 B2
(45) Date of Patent: Dec. 1, 2009

(54) METHOD FOR CLASSIFYING AND COUNTING LEUKOCYTES

(75) Inventors: Tomohiro Tsuji, Kobe (JP); Toshihiro Mizukami, Kobe (JP); Aya Konishi, Kobe (JP); Yusuke Mori, Kobe (JP); Yukie Nakazawa, Kobe (JP)

(73) Assignee: Sysmex Corporation, kobe-shi (JP)

( * ) Notice: Subject to any disclaimer, the term of this patent is extended or adjusted under 35 U.S.C. 154(b) by 698 days.

(21) Appl. No.: 10/517,422

(22) PCT Filed: Jun. 23, 2003

(86) PCT No.: PCT/JP03/07910

§ 371 (c)(1),
(2), (4) Date: Feb. 28, 2005

(87) PCT Pub. No.: WO04/001408

PCT Pub. Date: Dec. 31, 2003

(65) Prior Publication Data

US 2005/0202400 A1    Sep. 15, 2005

(30) Foreign Application Priority Data

Jun. 24, 2002  (JP) .............................. 2002-183259

(51) Int. Cl.
*C12N 13/00* (2006.01)
(52) U.S. Cl. ..................... 435/173.9; 436/63; 436/172
(58) Field of Classification Search ............. 435/173.9; 436/63, 172
See application file for complete search history.

(56) References Cited

U.S. PATENT DOCUMENTS

| | | | | | |
|---|---|---|---|---|---|
| 5,693,484 | A | * | 12/1997 | Nakamoto et al. ............. | 435/39 |
| 6,004,816 | A | * | 12/1999 | Mizukami et al. ............. | 436/10 |
| 2001/1004909 | | * | 12/2001 | Thompson et al. ............. | 435/4 |

FOREIGN PATENT DOCUMENTS

| | | | |
|---|---|---|---|
| EP | 0 617 281 | A2 | 9/1994 |
| EP | 0 844 481 | A1 | 5/1998 |
| JP | 5-99919 | A | 4/1993 |
| JP | 6-273413 | A | 9/1994 |
| JP | 7-503792 | A | 4/1995 |
| JP | 10-206423 | A | 8/1998 |
| JP | 2002-148261 | A | 5/2002 |

OTHER PUBLICATIONS

Oelschlaegel et al, "Flow cytometric DNA-quantification of three-color immunophenotyped cells for subpopulation specific determination of aneuploidy and proliferation," (J. of Immun. Methods), vol. 253, 2001, pp. 145-152.*
Diamond et al, "Flow Cytometry in the Diagnosis and Classification of Malignant Lymphoma and Leukemia", Cancer, Sep. 15, 1982, vol. 50, No. 6, pp. 1122-1135.
Petriz et al, "Relevance of Forward Scatter and Side Scatter in Aneuploidy Detection by Flow Cytometry", Analytical Cellular Pathology, vol. 10, No. 3, 1996, pp. 243-252.

* cited by examiner

*Primary Examiner*—Ralph Gitomer
(74) *Attorney, Agent, or Firm*—Sughrue Mion, PLLC

(57) ABSTRACT

There is provided a method for classifying and counting leukocytes with abnormal DNA amount, which comprises:
(1) a step of staining cells in a sample obtained from a hematological sample by treatment with a hemolytic agent to lyse erythrocytes, with a fluorescent dye which can make a difference in the fluorescence intensity at least among mature leukocytes, leukocytes with abnormal DNA amount and immature leukocytes;
(2) a step of introducing the sample containing the stained cells into a flow cytometer to measure scattered light and fluorescence of the respective cells;
(3) a step of classifying leukocytes and coincidence cells/platelet clumps utilizing a difference in the intensity of a scattered light peak and a difference in the scattered light width;
(4) a step of classifying and counting mature leukocytes, leukocytes with abnormal DNA amount and immature leukocytes, utilizing a difference in the scattered light intensity and a difference in the fluorescence intensity of leukocytes classified in the step (3).

10 Claims, 10 Drawing Sheets

Normal leukocytes   Leukocytes with
                    abnormal DNA amount

METHOD FOR CLASSIFYING AND COUNTING LEUKOCYTES

FIELD OF THE INVENTION

The present invention relates to a method for classifying and counting leukocytes. More particularly, it relates to a method for classifying and counting leukocytes, particularly leukocytes with abnormal DNA amount, in hematological samples utilizing a flow cytometer.

BACKGROUND ART

In the field of clinical laboratory test, classifying and counting leukocytes with abnormal DNA amount or immature leukocytes provide very useful information in diagnosis of diseases. For example, leukocytes in normal peripheral blood generally consist of these five-types, i.e., lymphocytes, monocytes, basophiles, eosinophils and neutrophils, and the DNA amount of leukocytes is constant. However, leukocytes with abnormal DNA amount appear, for example, in blood disorders such as viral diseases or lymphocytic leukemia, and immature leukocytes appear in such blood disorders as myclocytic leukemia.

Usually, in order to measure leukocytes with abnormal DNA amount, it is necessary to mix and stain mononuclear leukocytes (lymphocytes and monocytes), which are separated from leukocytes by specific gravity centrifugation, or peripheral blood with a nucleic acid-staining dye and a hemolytic agent, and subsequently to carry out the measurement. Separation of the mononuclear leukocytes by specific gravity centrifugation is complicated in operation and requires 1 hour or more for completion of the separation. In addition, 30 minutes or more are required for mixing and staining mononuclear leukocytes or peripheral blood with the nucleic acid-staining dye and the hemolytic agent.

In general, in order to classify and count immature leukocytes, a blood smear is prepared, properly stained and observed under a microscope for classification and count. On the other hand, in recent year, a variety of full-automatic hematocytometers have been provided utilizing the principle of a flow cyctometer. Although normal leukocytes can be highly precisely classified and counted with these cytometers, immature leukocytes can not precisely be detected and classified because the cytometers are greatly influenced by platelet clumps and coincidence cells.

On the other hand, it has been reported that immature leukocytes and normal leukocytes can be simultaneously classified and counted by maintaining the immature leukocytes in a viable state and treating other leukocytes with a hemolytic agent which damages other leukocytes; staining the damaged cells with a fluorescent dye which can stain the damaged cells; and measuring scattered light and fluorescence of the resulting blood corpuscles (Japanese Unexamined Patent Application Hei 10(1998)-206423). In this method, however, it was not possible to differentiate leukocytes with abnormal DNA amount from platelet clumps and coincidence cells, thus it was difficult to precisely classify and count leukocytes with abnormal DNA amount.

Thus, there is a need for a rapid, simple and highly precise method for measuring leukocytes with abnormal DNA amount and simultaneously, immature leukocytes.

DISCLOSURE OF THE INVENTION

According to the present invention, there is provided a method which makes it possible to classify and count leukocytes with abnormal DNA amount and, simultaneously, immature leukocytes and mature leukocytes, by maintaining immature leukocytes in a viable state, treating other leukocytes with a hemolytic agent which damages other leukocytes, staining the damaged cells with a fluorescent dye which can stain damaged cells, measuring scattered light and fluorescence of the resulting blood corpuscles, and using the difference in the intensity of the scattered light peak and the difference in the scattered light width.

Therefore, according to the invention, there is provided a method for classifying and counting leukocytes, which comprises:

(1) a step of staining cells in a sample obtained from a hematological sample by treatment with a hemolytic agent, with a fluorescent dye which can make a difference in the fluorescence intensity at least among mature leukocytes, leukocytes with abnormal DNA amount and immature leukocytes;

(2) a step of introducing the sample containing the stained cells into a flow cytometer to measure scattered light and fluorescence of the respective cells;

(3) a step of classifying leukocytes and coincidence cells/platelet clumps utilizing a difference in the intensity of a scattered light peak and a difference in the scattered light width;

(4) a step of classifying and counting mature leukocytes, leukocytes with abnormal DNA amount and immature leukocytes, utilizing a difference in the scattered light intensity and a difference in the fluorescence intensity of leukocytes classified in the step (3).

The term "hematological sample" as used herein refers to a body fluid sample containing leukocytes such as samples collected from peripheral blood, myelic needling fluid, urine, and the like.

The term "mature leukocytes" as used herein refers to mature lymphocytes, monocytes, and granulocytes.

The term "leukocytes with abnormal DNA amount" refers to leukocytes in which the amount of DNA is higher or lower than that in normal leukocytes. In the present invention, however, leukocytes with abnormal DNA amount mean leukocytes in which the amount of DNA is higher than that in the normal one.

The term "immature leukocytes" as used herein refers to immature leukocytes which exist usually in bone marrow and do not occur in the peripheral blood. These include, for example, myeloblasts, promyelocytes, myelocytes, metamyelocytes, and the like. In some cases, promyelocytes, myelocytes, and metamyelocytes are collectively called immature corpuscles of granulocytic series. In addition, hemopoietic precursor cells of leukocytic series such as myeloid series stem cells (CFU-GEMN), neutrophil-macrophage colony-forming cells (CFU-GM), eosinophil colony-forming cells (CFU-EOS), and the like, all of which are cells in the differentiation stage prior to blast cells are included in the scope of the immature leukocytes according to the invention.

The term "platelet clumps" as used herein refers to the one obtained by aggregation of two or more platelets.

The term "coincidence cells" as used herein refers to the state in which two or more cells pass at approximately the same time through the detection section of a flow cell and are counted as one cell.

The term "scattered light peak" as used herein refers to a peak of signal wave form obtained from scattered light, and the "scattered light width" refers to the width of signal wave form obtained from scattered light.

In present the invention, a hematological sample is treated with a hemolytic agent to lyse erythrocytes. On the other hand, by this treatment, immature leukocytes are not lysed or damaged, but mature leukocytes and leukocytes with abnormal DNA amount are damaged. When a hemolytic agent of a particular composition is allowed to act on cells, although the action mechanism is not clear, a part of the cell membrane lipid component of particular cells is extracted (withdrawn) to make a small hole on the cell membrane, through which a specific substance can pass. This is called damage. As a result, a dye molecule can penetrate into the particular cells to stain the same. Therefore, the damaged mature leukocytes and leukocytes with abnormal DNA amount are in a state suitable for staining. To the contrary, the undamaged immature leukocytes are not stained by the dye because no hole is made through which the dye is allowed to pass. Additionally, in the mature leukocytes and leukocytes with abnormal DNA amount, the amount of the dye to be bound depends on the amount of DNA contained in each cell. Therefore, when such cells are stained with the dye, the amount of the dye involved in staining is varied depending on the DNA amount, resulting in a difference in the intensity of fluorescence from the stained cells. For example, in case of leukocytes with abnormal DNA amount which contain twice higher amount of DNA compared to mature leukocytes, the amount of the dye to be bound is twice higher than the normal mature leukocytes, thus these cells generate stronger fluorescence than the mature leukocytes. As a result, there can be produced a difference in the intensity of fluorescence among mature leukocytes, leukocytes with abnormal DNA amount and immature leukocytes.

The hemolytic agent used in the step (1) of the invention preferably comprises a surfactant, a solubilizing agent, amino acid(s), and a buffer.

As a surfactant, a variety of agents can be employed, and preferred is a polyoxyethylene nonionic surfactant. Specifically, it includes those having the following formula (II):

$$R^{1II}-R^{2II}-(CH_2CH_2O)_{n_{II}}-H \tag{II}$$

(wherein $R^{1II}$ represents a $C_{9-25}$ alkyl, alkenyl or alkynyl group; $R^{2II}$ represents —O—,

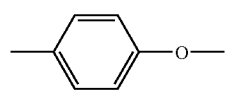

or —COO—; and $n_{II}$ is 10-40).

The $C_{9-25}$ alkyl group includes nonyl, decyl, undecyl, dodecyl, tridecyl, tetradecyl, and the like. The $C_{9-25}$ alkenyl group includes dodecenyl, tetradecenyl, and the like. The $C_{9-25}$ alknyl group includes dodecynyl, undecynyl, dodecynyl, and the like.

More specifically, polyoxyethylene(20)lauryl ether, polyoxyethylene(15)oleyl ether, and polyoxyethylene(16)oleyl ether are preferred.

The surfactant may be used in the form of aqueous solution. For example, the concentration of the polyoxyethylene nonionic surfactant in water depends on the type of the surfactant used, however, may be in the range of 0.1-2.0 g/L (preferably, 0.5-1.5 g/L) for polyoxyethylene(20)lauryl ether, 1-9 g/L (preferably, 3-7 g/L) for polyoxyethylene(15)oleyl ether, and 5-50 g/L (preferably, 15-35 g/L) for polyoxyethylene(16)oleyl ether. The polyoxyethylene nonionic surfactant, when the carbon number of the hydrophobic group is the same, shows a more potent cell-damaging property with decrease of the number of $n_{II}$, and this potency decreases with increase of the number of $n_{II}$. In addition, when the number of $n_{II}$ is the same, the cell-damaging potency increases with decrease of the carbon number of the hydrophobic group. In consideration of this point of view, the concentration required for a surfactant may easily be determined by an experiment using the above-mentioned values as standards.

The solubilizing agent is used to give damage to the cell membrane of blood corpuscles and reduce their size. Specifically, one or more selected from the followings:

sarcosine derivatives of the formula (III):

(III)

(wherein $R^{1III}$ is a $C_{10-22}$ alkyl group; and $n^{III}$ is 1-5)

or salts thereof;

cholic acid derivatives of the formula (IV):

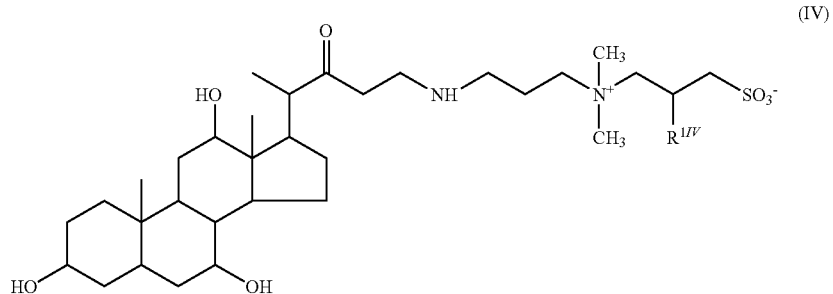

(IV)

(wherein $R^{1IV}$ is a hydrogen atom or a hydroxy group); and methylglucanamides of the formula (V):

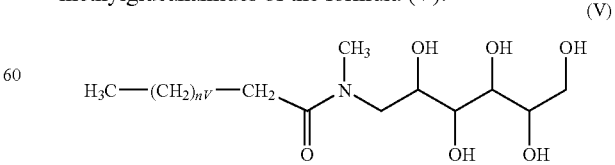

(V)

(wherein $n^V$ is 5-7)

may be used.

The $C_{10-22}$ alkyl group includes decyl, dodecyl, tetradecyl, oleyl, and the like.

Specifically, sodium N-lauroylsarcosinate, sodium lauroyl methyl β-alanine, lauroylsarcosine, CHAPS (3-[(3-cholamidopropyl)dimethylammonio]-1-propanesulfonate), CHAPSO (3-[(3-cholamidopropyl)dimethylammonio]-2-hydroxy-1-propanesulfonate), MEGA8 (octanoyl-N-methylglucamide), MEGA9 (nonanoyl-N-methylglucamide), MEGA10 (decanoyl-N-methylglucamide), and the like are preferably used.

The concentration of the solubilizing agent is preferably 0.2-2.0 g/L for sarcosine acid derivatives or their salts, 0.1-0.5 g/L for cholic acid derivatives, and 1.0-8.0 g/L for methylglucanamide.

In addition, n-octyl β-glucoside, sucrose monocaprate, N-formylmethylleucylalanine and the like can be used as solubilizing agents, which may preferably be used in a concentration of 0.01-50.0 g/L.

The amino acid is used to immobilize the cytoplasm and cell membrane of immature leukocytes. For example, it is possible to use amino acids which constitute proteins, preferably glutamic acid, valine, particularly sulfur-containing amino acids such as methionine, cystine and cysteine are used; and most preferred is methionine. The amino acid may be used in the range of 1-50 g/L; preferably 8-12 g/L for glutamic acid, and 16-24 g/L for methionine.

As for the buffer, Good buffer such as HEPES or phosphate buffer may preferably be added with a pH adjusting agent such as sodium hydroxide, and if necessary, with an osmotic pressure adjusting agent such as sodium chloride to obtain pH of 5.0-9.0 and an osmotic pressure of 150-600 mOsm/kg.

As for the hemolytic agent according to the present invention, it is preferable to use the hemolytic agent described in Japanese Unexamined Patent Publication No. Hei 6(1994)-273413 which comprises (1) a polyoxyethylene nonionic surfactant; (2) a solubilizing agent to give damage to cell membrane of blood corpuscles and reduce their size; (3) an amino acid; and (4) a buffer by which pH and osmotic pressure of the liquid are adjusted to 5.0-9.0 and 150-600 mOsm/kg, respectively, and a buffer by which the conductivity is adjusted to 6.0-9.0 mS/cm.

The fluorescent dye according to the invention which can make a difference in the fluorescence intensity among mature leukocytes, leukocytes with abnormal DNA amount and immature leukocytes may be any kind as far as it can stain either of damaged cells or immature leukocytes. The dye which can stain damaged cells is preferred. Such a dye can stain all of the cells including blood corpuscles in the sample.

The dye which can stain damaged cells includes dyes which have specificity to cell nuclei, particularly DNA, or dyes which have specificity to RNA. For this purpose, some cationic dyes are preferably used.

In general, the cationic dye passes through a cell membrane of a viable cell to stain the intracellular component. It has been well known, however, that certain cationic dyes (for example, ethidium bromide, propidium iodide, etc.) do not pass through viable cells and can stain only damaged cells.

Specifically, the fluorescence dye includes the above-mentioned ethidium bromide and propidium iodide as well as ethidium-acridine heterodimer (commercially available from Molecular Probes), ethidium azide, ethidium homodimer-1, ethidium homodimer-2, ethidium monoazide, TOTO-1, TO-PRO-1, TOTO-3, and TO-PRO-3. When a He—Ne or red semiconductor laser is used as a light source, a dye represented by the formula (I):

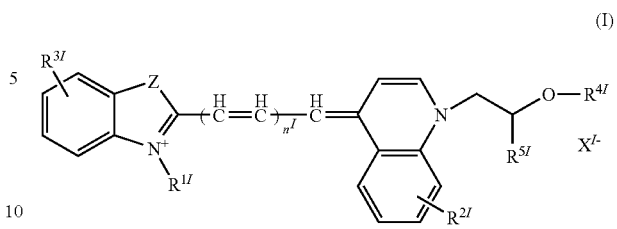

(I)

(wherein $R^{1I}$ is a hydrogen atom or a lower alkyl group; $R^{2I}$ and $R^{3I}$ each is a hydrogen atom, a lower alkyl group or a lower alkoxy group; $R^{4I}$ is a hydrogen atom, an acyl group or a lower alkyl group; $R^{5I}$ is a hydrogen atom or a lower allyl group which may be substituted; Z is sulfur atom, oxygen atom, or carbon atom which is substituted by a lower alkyl group; $n^I$ is 1 or 2; and $X^{I-}$ is an anion)

may be used as a suitable dye.

The lower alkyl group with regard to $R^{1I}$ of the above formula means a $C_{1-6}$ straight or branched alkyl group. It includes methyl, ethyl, propyl, butyl, isobutyl, sec-butyl, tert-butyl, pentyl, and hexyl groups and particularly, methyl and ethyl groups are preferred.

The lower alkyl group with regard to $R^{2I}$ and $R^{3I}$ includes the same groups as the above; and the lower alkoxy group means a $C_{1-6}$ alkoxy group and includes, for example methoxy, ethoxy, propoxy, and the like; and particularly methoxy and ethoxy groups are preferred.

The acyl group with regard to $R^{4I}$ is preferably an acyl group derived from an aliphatic carboxylic acid and includes, for example, acetyl, propionyl, and the like; and particularly, acetyl group is preferred. The lower alkyl group includes the same groups as the above.

The lower alkyl group with regard to $R^{5I}$ includes the same groups as the above; the lower alkyl group which may optionally be substituted means the lower alkyl group which may be substituted by 1 to 3 hydroxy group(s), halogen atom (fluorine, chlorine, bromine or iodine) and the like; and particularly, methyl and ethyl groups substituted by one hydroxy group are preferred.

The lower alkyl group with regard to Z includes the same groups as the above; and as Z, a sulfur atom is preferred.

The anion with regard to $X^{I-}$ includes halogen ions (fluorine, chlorine, bromine or iodine ion), boron halide ions ($BF_4^-$, $BCl_4^-$, $BBr_4^-$, etc.), phosphorus compound ions, halogeno-oxygen acid ions, fluorosulfuric acid ions, methyl sulfate ions, and tetraphenyl boron compound ions which have a halogen or halogeno-alkyl group as a substituent on the aromatic rings. Particularly, bromine ion or $BF_4^-$ is preferred.

The above-mentioned dyes may be used alone or in combination of two or more species. A specific example of the above-mentioned dyes preferably includes those as described below, without limiting the present invention.

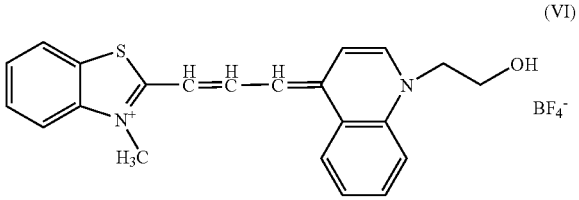

(VI)

-continued

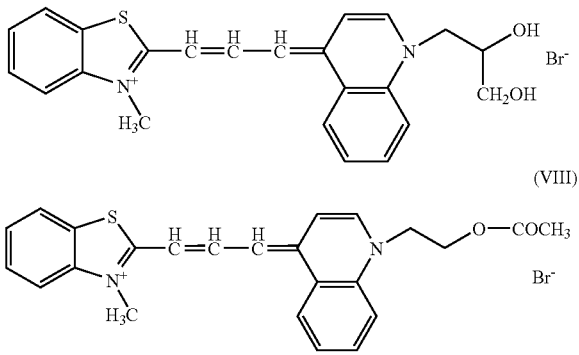

In a preferred embodiment of the step (1), a solution containing the hemolytic agent and the fluorescence dye is mixed with a hematological sample. Alternatively, the fluorescence dye may be dissolved, in advance, to an aqueous organic solvent such as ethylene glycol and mixed with the hemolytic agent upon use. This case is preferable because the storage stability of the dye can be improved. The concentration of the dye may suitably be decided depending on the species of the dye to be used. For example, ethidium bromide may be used in the range of 0.01-100 mg/L, preferably 0.1-30 mg/L.

Mixing of the hematological sample with the hemolytic agent containing the fluorescence dye may preferably be carried out at a ratio of hematological sample: hemolytic agent containing a fluorescence dye=1:10-1:1000, at a temperature of 20-40° C. for a reaction period of 5 seconds to 5 minutes. When the reaction temperature is high, it is preferred to reduce the reaction time. In the invention, the measurement of the amount of DNA in a sample containing immature leukocytes can be effected by extending the reaction time in order to stain immature leukocytes. In this case, the reaction time is preferably in a period of, for example, 10 seconds to 5 minutes.

In the step (2), thus prepared sample for measurement is introduced into a flow cytometer, in which scattered light and fluorescence of the respective stained cells in the sample are measured.

FIG. 18 shows an oblique perspective figure illustrating an optical system of flow cytometer which can be used in the invention. In this figure, a beam emitted from a laser 21 irradiates an orifice portion of a sheath flow cell 23 through a collimator lens 22. The forward scattered light emitted by the blood corpuscles passing through the orifice portion is introduced into a photodiode 26 through a condensing lens 24 and a pin hole plate 25.

On the other hand, with regard to side scattered light and side fluorescence emitted by the blood corpuscles passing through the orifice portion, the side scattered light is introduced into a photomultiplier tube (hereinafter referred to as "photomul") 29 through a condensing lens 27 and a dichroic mirror 28, and the side fluorescence is introduced into a photomul 31 through the condensing lens 27, the dichroic mirror 28, a filter 29 and a pin hole plate 30.

The forward scattered light signal generated by the photodiode 26, the side scattered light signal generated by the photomul 29, and the side fluorescence signal generated by the photomul 31 are amplified by amplifiers 32, 33, and 34, respectively, and input an analyzing part 35.

The term "scattered light" as used herein refers to scattered light which can be measured with a commercially available flow cytometer, and includes forward low angle scattered light (for example, receiving angle less than 0-5°), forward high angle scattered light (for example, receiving angle around 5-20°), and side scattered light, and preferably forward low angle scattered light and, as further scattered light, side scattered light are chosen. The side scattered light reflects intracellular information such as a nuclear form.

As for fluorescence, a suitable receiving wavelength is selected according to the dye used. The fluorescent signals reflect chemical properties of cells.

The light source of flow cytometer is not particularly limited, and is selected from the sources having a suitable wavelength for excitation of the dye. For example, argon laser, He—Ne laser, red semiconductor laser, blue semiconductor laser, and the like may be used. In particular, a semiconductor laser is much cheaper than gas laser, thus cost for an apparatus can be reduced drastically.

In the step (3), platelet clumps/coincidence cells and leukocytes are classified using the difference in the intensity of the scattered light peak and the difference in the scattered light width. Specifically, for example, a scattergram is prepared in which the X-axis indicates the forward scattered light width and the Y-axis indicates the forward scattered light peak. As shown in FIG. 1, for example, platelet clumps and coincidence cells as well as leukocytes and ghost form respective groups which distribute in the scattergram. From all of the cells on the scattergram, the platelet clumps and coincidence cells are removed to classify the platelet clumps/coincidence cells and the leukocytes/ghost. By this operation, it is possible to prevent an appearance of platelet clumps and coincidence cells in the area of the leukocytes with abnormal DNA amount, and to precisely classify and count leukocytes with abnormal DNA amount.

Subsequently, in the step (4), mature leukocytes, leukocytes with abnormal DNA amount and immature leukocytes are classified and counted utilizing the difference in the scattered light intensity, and the difference in the fluorescence intensity of the components classified in the step (3). Specifically, for example, a scattergram, in which the X-axis indicates the fluorescence intensity and the Y-axis indicates the forward scattered light intensity, is prepared only with groups of the blood corpuscle components excluding the above-mentioned platelet clumps and coincidence cells. As shown in FIG. 2, for example, respective groups of mature leukocytes, leukocytes with abnormal DNA amount and immature leukocytes as well as the group formed of erythrocyte ghost, respectively, are distributed in the scattergram. The areas of the respective groups are established using a suitable analyzing software, and the cells included in those areas are classified and counted. Thus, the number of mature leukocytes, the number of immature leukocytes and the number of leukocytes with abnormal DNA amount can be obtained.

Further, in the step (5), the ratio of the mature leukocytes or immature leukocytes relative to the leukocytes with abnormal DNA amount is calculated from the number of leukocytes with abnormal DNA amount and the number of mature leukocytes or the number of immature leukocytes.

Further, in the step (6), the ratio of the immature leukocytes relative to the mature leukocytes is calculated from the number of mature leukocytes and the number of immature leukocytes.

Further, in the step (7), different kind of scattered light is further measured in the step (2), and a scattergram is prepared using differences of the scattered light intensity and fluorescence intensity of the mature leukocytes obtained in the step (4). For example, a scattergram as shown in FIG. 3, in which the X-axis indicates the intensity of red fluorescence and the Y-axis indicates the intensity of side scattered light, is prepared. In the scattergram, at least 3 species, for example, lymphocytes, monocytes and granulocytes form respective groups, and are distributed. The areas of the respective groups are established using a suitable analyzing software, and the cells included in those areas are classified and counted. Thus, lymphocytes, monocytes and granulocytes can be classified and counted.

Further, in the step (8), different kind of scattered light is further measured in the step (2), and a scattergram is prepared using differences of the scattered light intensity and fluorescence intensity of the immature leukocytes obtained in the step (4). For example, a scattergram as shown in FIG. 3, in which the X-axis indicates the intensity of red fluorescence and the Y-axis indicates the intensity of side scattered light, is prepared. In the scattergram, at least 2 species, for example, myeloblasts and immature corpuscles of granulocytic series form respective groups, and are distributed. The areas of the respective groups are established using a suitable analyzing software, and the cells included in those areas are classified and counted. Thus, myeloblasts and immature corpuscles of granulocytic series can be classified and measured.

In this connection, the steps (7) and (8) may be carried out separately or simultaneously. When both steps are carried out simultaneously, it is preferable to prepare a scattergram using the difference in the scattered light intensity and the difference in the fluorescence intensity of the components being removed of ghost in the step (4), since a scattergram as shown in FIG. 3 is obtained and the mature leukocytes and immature leukocytes can be classified into further multiple groups and counted.

EMBODIMENTS OF THE INVENTION

The present invention will be explained by the following examples in more detail. A variety of alteration and modification can be applied to the invention, and accordingly, the scope of the invention is not limited by the following examples.

Example 1

A reagent comprising an aqueous solution of the following composition was prepared.

| (The present method) | |
|---|---|
| Polyoxyethylene(16)oleyl ether | 24.0 g |
| Sodium N-lauroylsarcosinate | 1.5 g |
| DL-Methionine | 20.0 g |
| 1N-NaOH | 0.3 g |
| NaCl | 4.0 g |
| Dye of formula (VI) | 3.0 mg |
| HEPES | 12.0 g |
| Pure water | 1000 ml |

The above-mentioned reagent (1 ml) was mixed with 33 μl of blood collected from a patient suffering from lymphoid leukemia, and after a lapse of 10 seconds, forward low angle scattered light, side scattered light, and red fluorescence were measured with a flow cytometer (light source: red semiconductor laser, wavelength: 633 nm).

| (A standard method for measurement of the DNA amount) | |
|---|---|
| Trisodium citrate | 100 mg |
| Triton X-100 (Wako Pure Chemical Industries, Ltd.) | 0.2 g |
| Propidium iodide (Sigma) | 0.2 g |
| RO water | 100 ml |

The above-mentioned reagent (1 ml) was mixed with 100 μl of blood collected from the above-mentioned patient, and after a lapse of 30 minutes, red fluorescence was measured with a flow cytometer (light source: argon ion laser, wavelength: 488 nm).

Figure 1:
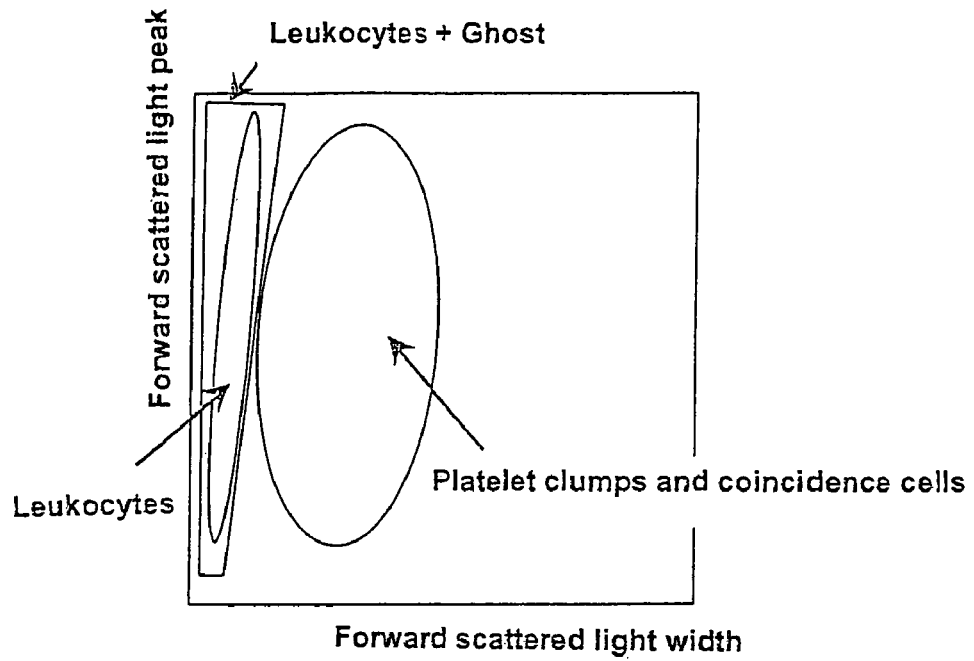
FIG. 1 is a conceptual illustration showing the positions at which the respective cells appear as classified and counted according to the method of the invention.
Figure 2:
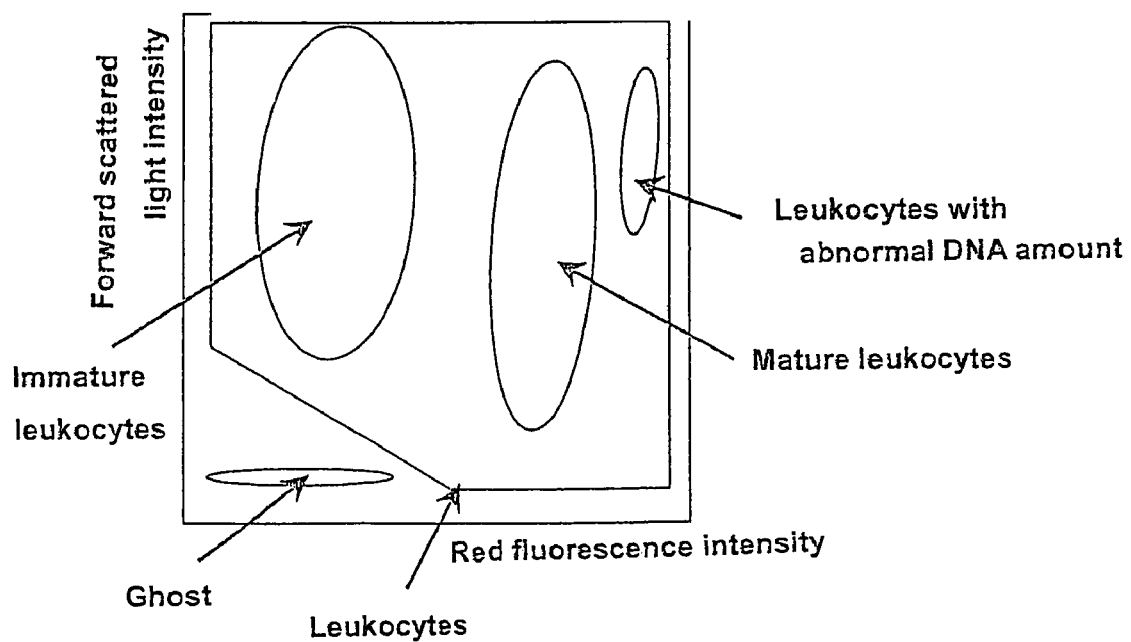
FIG. 2 is a conceptual illustration showing the positions at which the respective cells appear as classified and counted according to the method of the invention.
Figure 3:
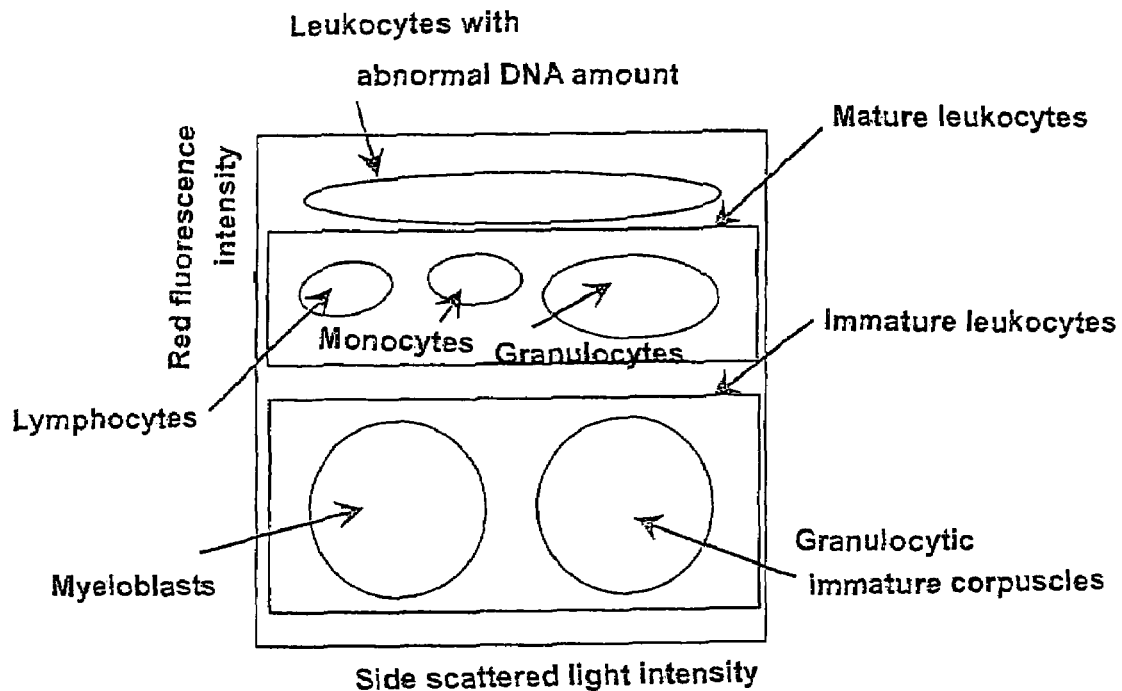
FIG. 3 is a conceptual illustration showing the positions at which the respective cells appear as classified and counted according to the method of the invention.
Figure 4:
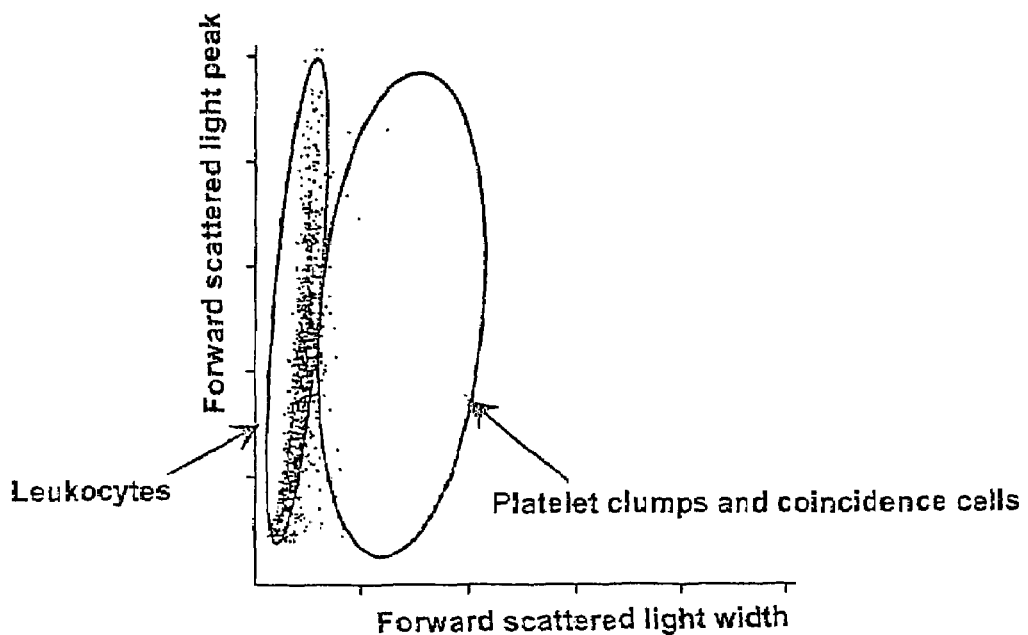
FIG. 4 is a scattergram of Example 1 in which the X-axis indicates the forward low angle scattered light width and the Y-axis indicates the forward low angle scattered light peak.
Figure 5:
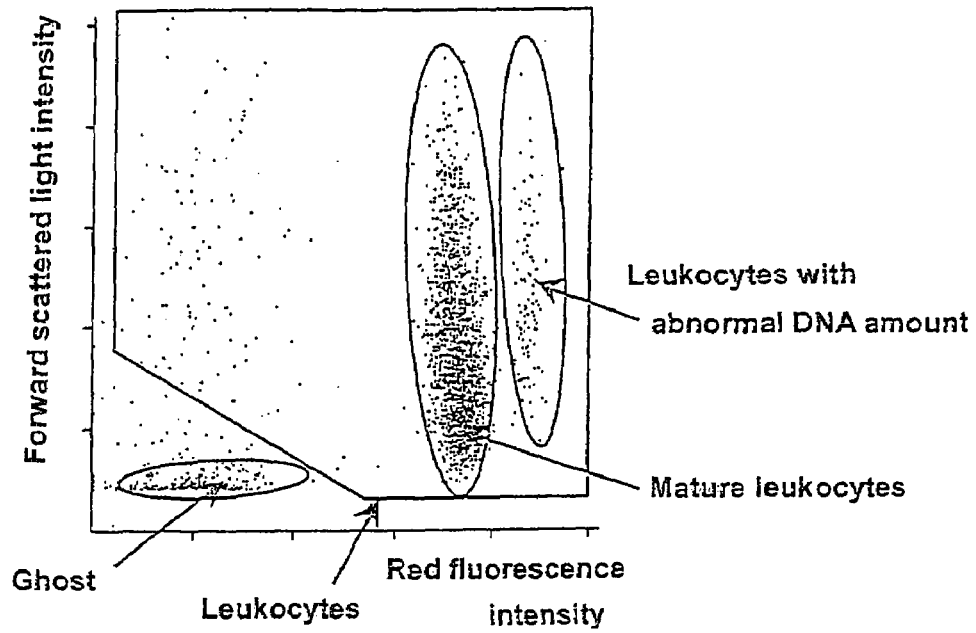
FIG. 5 is a scattergram of Example 1 in which the X-axis indicates the red fluorescence intensity and the Y-axis indicates the forward low angle scattered light intensity.
Figure 6:
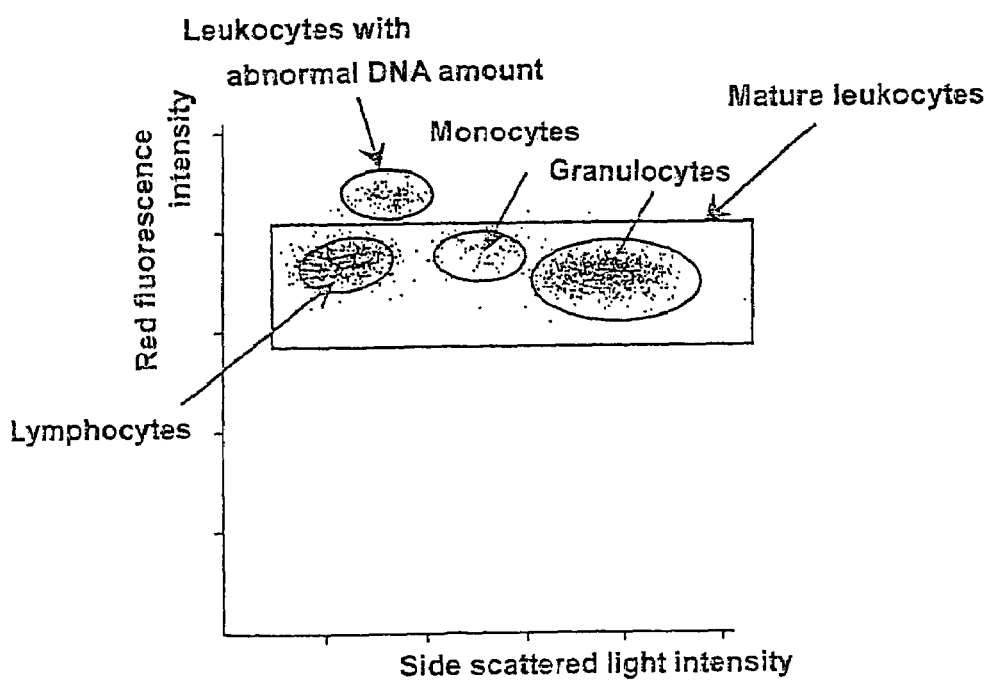
FIG. 6 is a scattergram of Example 1 in which the X-axis indicates the side scattered light intensity and the Y-axis indicates the red fluorescence intensity.

The results are shown in a scattergram (FIG. 4) in which the X-axis indicates the forward low angle scattered light width and the Y-axis indicates the forward low angle scattered light peak, a scattergram (FIG. 5) in which the X-axis indicates the red fluorescence intensity and the Y-axis indicates the forward low angle scattered light intensity, and a scattergram (FIG. 6) in which the X-axis indicates the side scattered light intensity and the Y-axis indicates the red fluorescence intensity.

Figure 7:
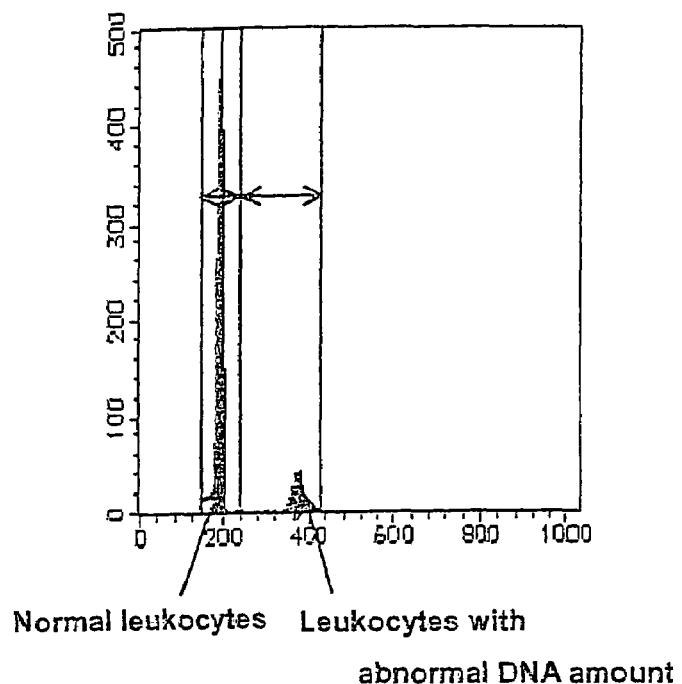
FIG. 7 represents results from the present method and from a standard method for measurement of the DNA amount.

The above-mentioned blood was stained by May-Grünwald stain and observed visually under a microscope. Leukocytes were classified into lymphocytes, monocytes and granulocytes. In addition, using the above-mentioned blood, the DNA amount of leukocytes was determined by a flow cytometer according to the standard method for measurement of the DNA amount. The results are shown in Table 1 and FIG. 7.

TABLE 1

Results by the present method and by the visual observation

|  | Present method | Visual method |
|---|---|---|
| Lymphocyte (%) | 38.3 | 39.0 |
| Monocyte (%) | 4.5 | 3.0 |
| Granulocyte (%) | 47.7 | 49.0 |
| Myeloblast (%) | 2.3 | 1.5 |
| Granulocytic series immature corpuscle (%) | 2.1 | 1.5 |
| Leukocyte with abnormal DNA amount (%) | 5.1 | 6.0 |
| Mature leukocyte: Leukocyte with abnormal DNA amount | 17.7:1 | 15.2:1 |
| Immature leukocyte: Leukocyte with abnormal DNA amount | 0.86:1 | 0.5:1 |
| Mature leukocyte: Immature leukocyte | 20.6:1 | 30.3:1 |

From the above results, it was shown that by the method of the invention, it is possible to measure leukocytes with abnormal DNA amount and immature leukocytes at the same time as the similar level as that of visual observation in a rapid, simple and highly precise way.

Example 2

A reagent comprising an aqueous solution of the following composition was prepared.

| (The present method) | |
|---|---|
| Polyoxyethylene(16)oleyl ether | 24.0 g |
| Sodium N-lauroylsarcosinate | 1.5 g |
| DL-Methionine | 20.0 g |
| 1N-NaOH | 0.3 g |
| NaCl | 4.0 g |
| Dye of formula (VII) | 3.0 mg |
| HEPES | 12.0 g |
| Pure water | 1000 ml |

The above-mentioned reagent (1 ml) was mixed with 33 μl of blood collected from a patient suffering from acute myelocytic leukemia (AML), and after a lapse of 10 seconds, forward low angle scattered light, side scattered light, and red fluorescence were measured with a flow cytometer (light source: red semiconductor laser, wavelength: 633 nm).

| (A standard method for measurement of the DNA amount) | |
|---|---|
| Trisodium citrate | 100 mg |
| Triton X-100 (Wako Pure Chemical Industries, Ltd.) | 0.2 g |
| Propidium iodide (Sigma) | 0.2 g |
| RO water | 100 ml |

The above-mentioned reagent (1 ml) was mixed with 100 μl of blood collected from the above-mentioned patient, and after a lapse of 30 minutes, red fluorescence was measured with a flow cytometer (light source: argon ion laser, wavelength: 488 nm).

Figure 8:
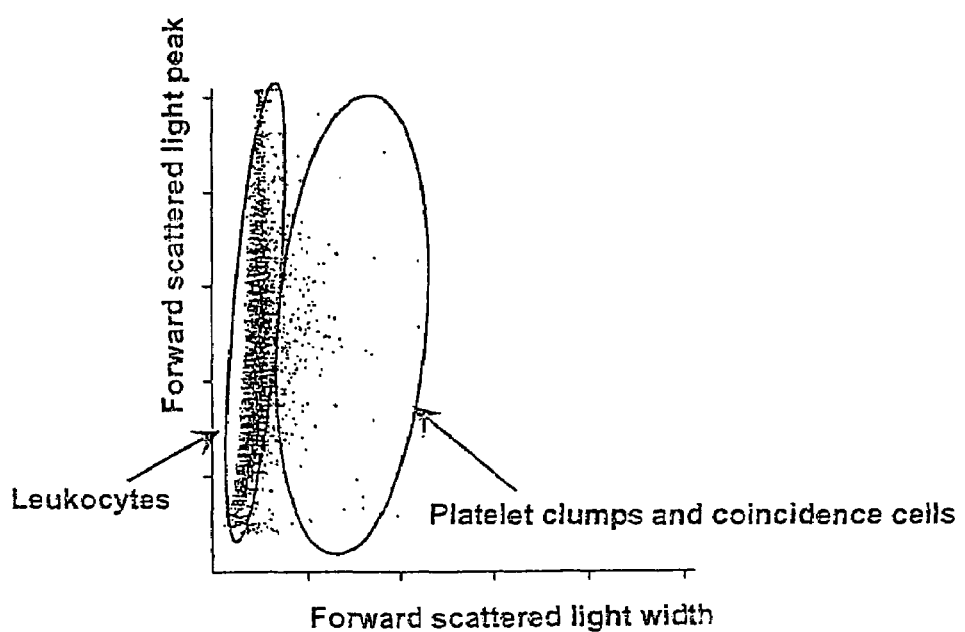
FIG. 8 is a scattergram of Example 2 in which the X-axis indicates the forward low angle scattered light width and the Y-axis indicates the forward low angle scattered light peak.
Figure 9:
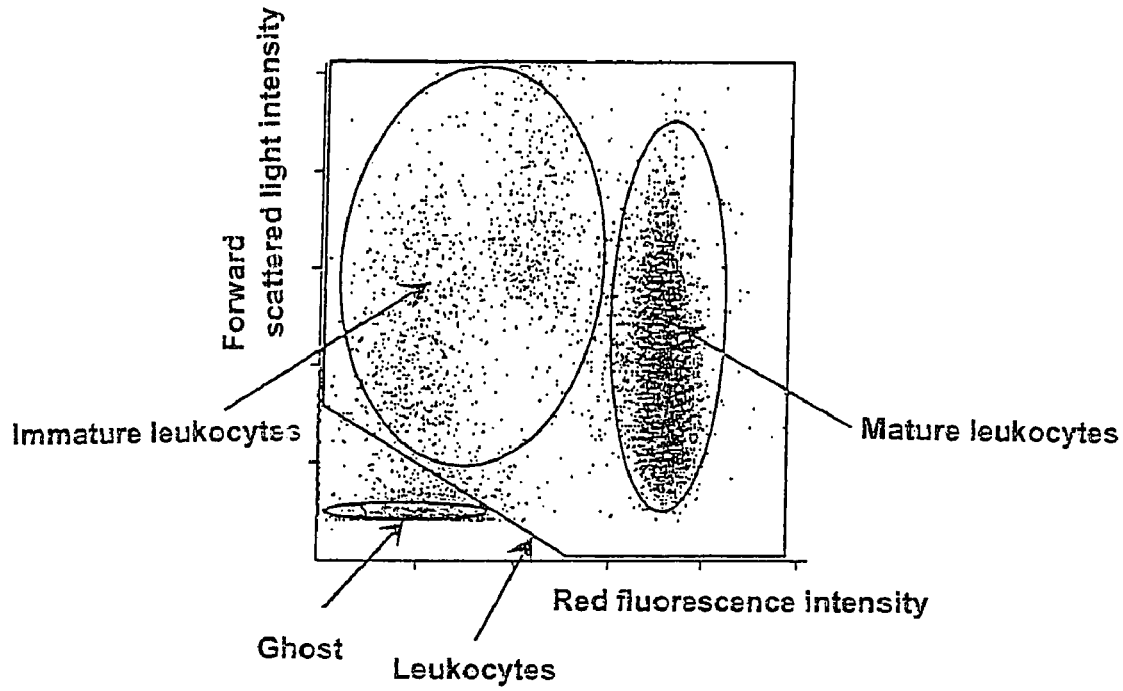
FIG. 9 is a scattergram of Example 2 in which the X-axis indicates the red fluorescence intensity and the Y-axis indicates the forward low angle scattered light intensity.
Figure 10:
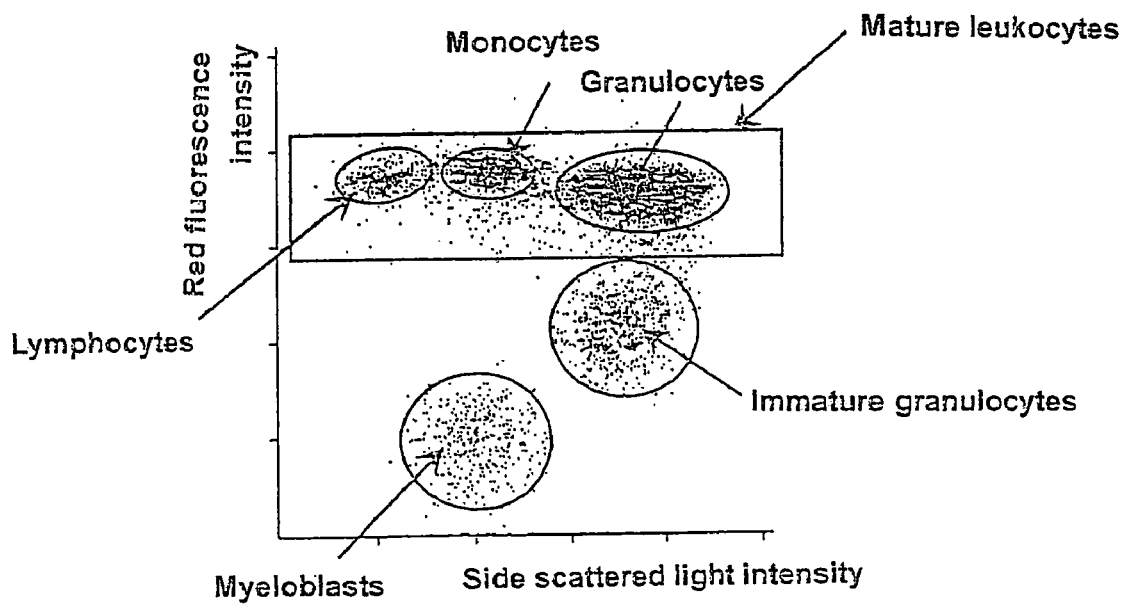
FIG. 10 is a scattergram of Example 2 in which the X-axis indicates the side scattered light intensity and the Y-axis indicates the red fluorescence intensity.

The results are shown in a scattergram (FIG. 8) in which the X-axis indicates the forward low angle scattered light width and the Y-axis indicates the forward low angle scattered light peak, a scattergram (FIG. 9) in which the X-axis indicates the red fluorescence intensity and the Y-axis indicates the forward low angle scattered light intensity, and a scattergram (FIG. 10) in which the X-axis indicates the side scattered light intensity and the Y-axis indicates the red fluorescence intensity.

The above-mentioned blood was stained by May-Grünwald stain and observed visually under a microscope. The leukocytes were classified into lymphocytes, monocytes and granulocytes. The results are shown in Table 2.

TABLE 2

|  | Present method | Visual method |
|---|---|---|
| Lymphocyte (%) | 3.6 | 4.0 |
| Monocyte (%) | 8.6 | 10.0 |
| Granulocyte (%) | 77.0 | 75.0 |
| Myeloblast (%) | 3.6 | 5.0 |
| Granulocytic immature corpuscle (%) | 7.2 | 6.0 |
| Leukocyte with abnormal DNA amount (%) | 0.0 | 0.0 |
| Mature leukocyte: Leukocyte with abnormal DNA amount | 89.2:0 | 89.0:0 |
| Immature leukocyte: Leukocyte with abnormal DNA amount | 10.8:0 | 11.0:0 |
| Mature leukocyte: Immature leukocyte | 8.26:1 | 8.1:1 |

From the above results, it was shown that by the method of the invention, it is possible to measure leukocytes with abnormal DNA amount and immature leukocytes at the same time in a rapid, simple and highly precise way.

Example 3

The reagents with the same composition as in Example 1 were used. The reagent of the present method (1 ml) was mixed with 33 μl of bone marrow fluid collected from a patient suffering from osteomyelodysplasia syndrome, and after a lapse of 7 seconds and 13 seconds, forward low angle scattered light, side scattered light, and red fluorescence were measured with a flow cytometer (light source: red semiconductor laser, wavelength: 633 nm).

(A standard Method for Measurement of the DNA Amount)

The reagent (1 ml) for the standard method for measurement of the DNA amount was mixed with 100 μl of bone marrow fluid collected from the above-mentioned patient, and after a lapse of 30 minutes, red fluorescence was measured with a flow cytometer (light source: argon ion laser, wavelength: 4-88 nm).

Figure 11:
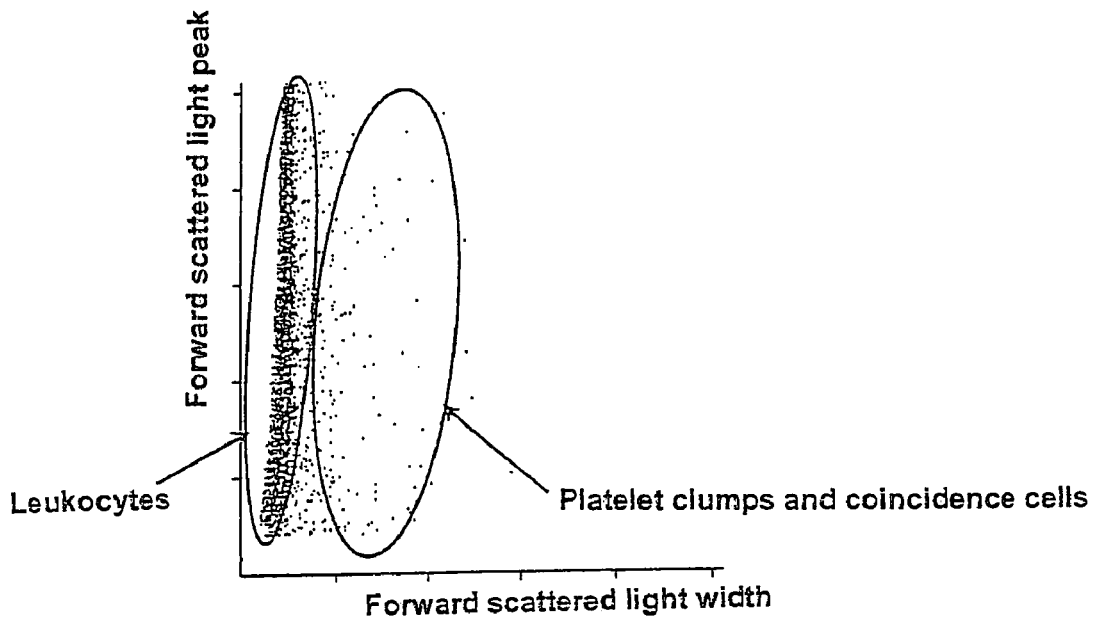
FIG. 11 is a scattergram of Example 3 depicted for 7 seconds of the reaction time in Example 3, in which the X-axis indicates the forward low angle scattered light width and the Y-axis indicates the forward low angle scattered light peak.
Figure 12:
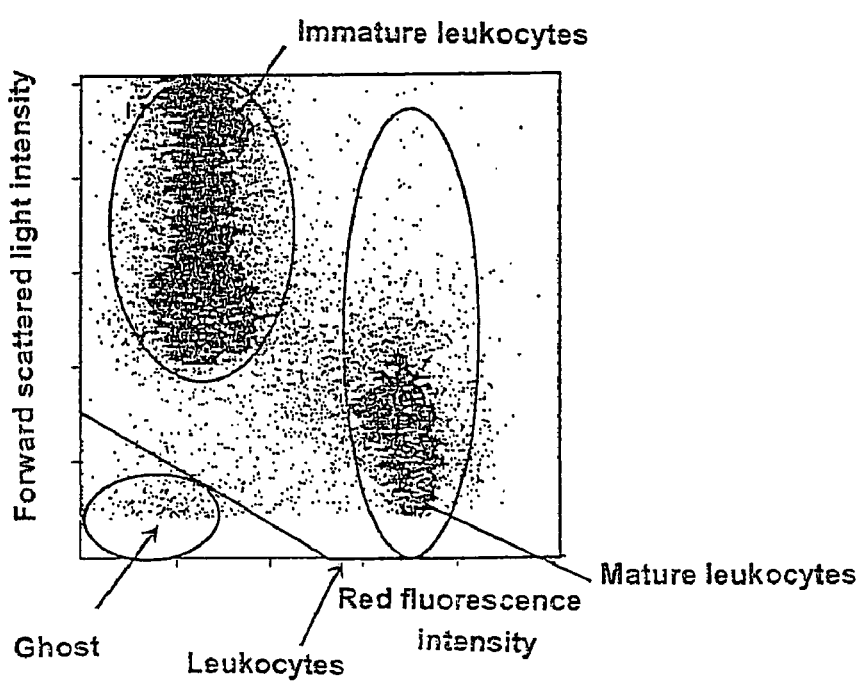
FIG. 12 is a scattergram depicted for 7 seconds of the reaction time in Example 3, in which the X-axis indicates the red fluorescence intensity and the Y-axis indicates the forward low angle scattered light intensity.
Figure 13:
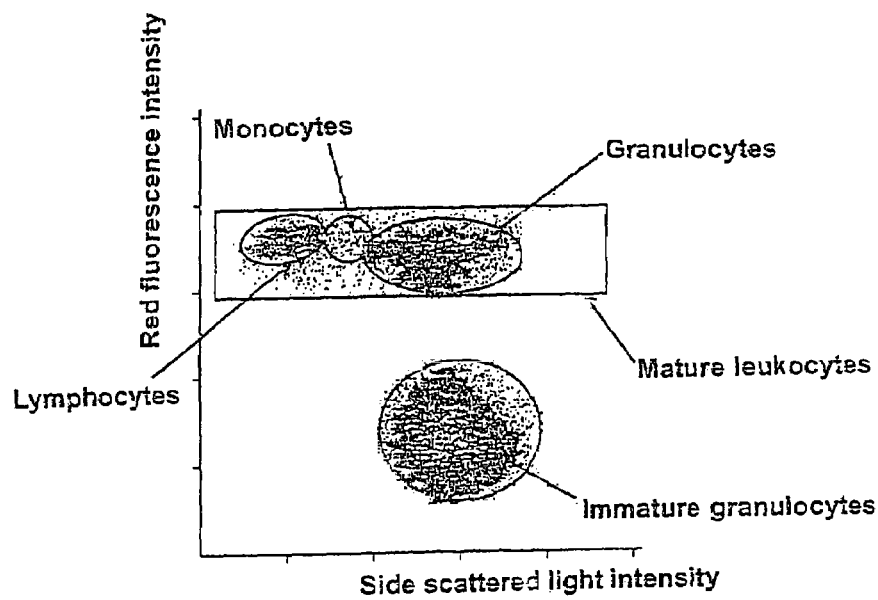
FIG. 13 is a scattergram depicted for 7 seconds of the reaction time in Example 3, in which the X-axis indicates the side scattered light intensity and the Y-axis indicates the red fluorescence intensity.
Figure 14:
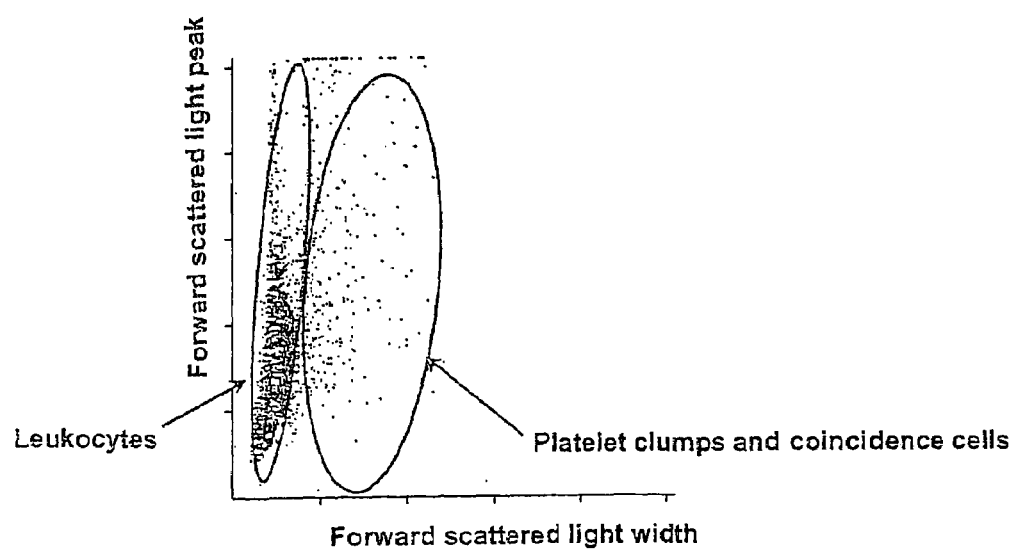
FIG. 14 is a scattergram depicted for 13 seconds of the reaction time in Example 3, in which the X-axis indicates the forward low angle scattered light width and the Y-axis indicates the forward low angle scattered light peak.
Figure 15:
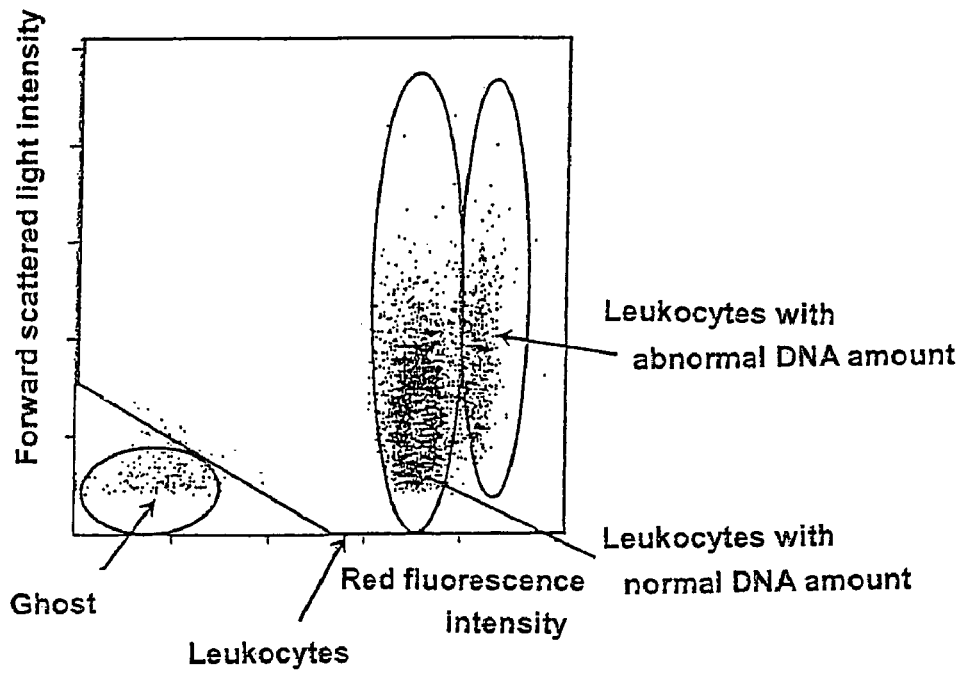
FIG. 15 is a scattergram depicted for 13 seconds of the reaction time in Example 3, in which the X-axis indicates the red fluorescence intensity and the Y-axis indicates the forward low angle scattered light intensity.
Figure 16:
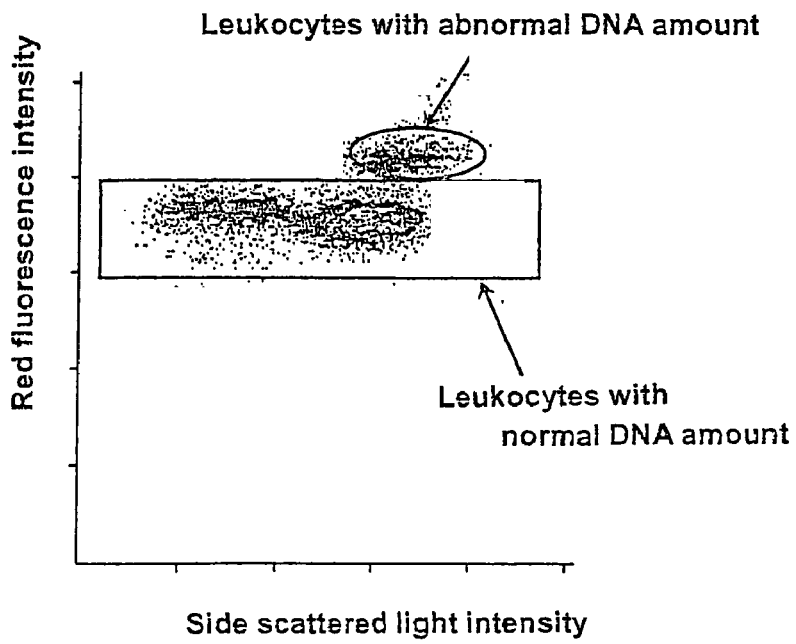
FIG. 16 is a scattergram depicted for 13 seconds of the reaction time in Example 3, in which the X-axis indicates the side scattered light intensity and the Y-axis indicates the red fluorescence intensity.

The results are shown in a scattergram (FIG. 11) for the case of 7 seconds of the reaction time in which the X-axis indicates the forward low angle scattered light width and the Y-axis indicates the forward low angle scattered light peak, a scattergram (FIG. 12) for the case of 7 seconds of the reaction time in which the X-axis indicates the red fluorescence intensity and the Y-axis indicates the forward low angle scattered light intensity, a scattergram (FIG. 13) for the case of 7 seconds of the reaction time in which the X-axis indicates the side scattered light intensity and the Y-axis indicates the red fluorescence intensity, a scattergram (FIG. 14) for the case of 13 seconds of the reaction time in which the X-axis indicates the forward low angle scattered light width and the Y-axis indicates the forward low angle scattered light peak, a scattergram (FIG. 15) for the case of 13 seconds of the reaction time wherein the X-axis indicates the red fluorescence intensity and the Y-axis indicates the forward low angle scattered light intensity, and a scattergram (FIG. 16) for the case of 13 seconds of the reaction time in which the X-axis indicates the side scattered light intensity and the Y-axis indicates the red fluorescence intensity.

Figure 17:
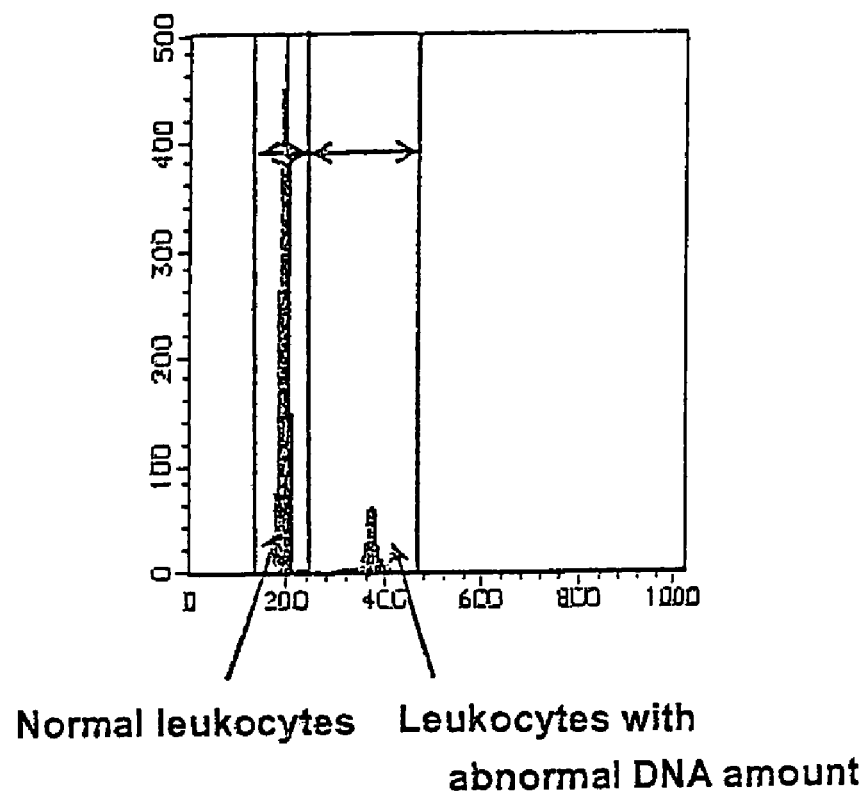
FIG. 17 represents results from the present method, in which the reaction time is 13 seconds, and from a standard method for measurement of the DNA amount.
Figure 18:
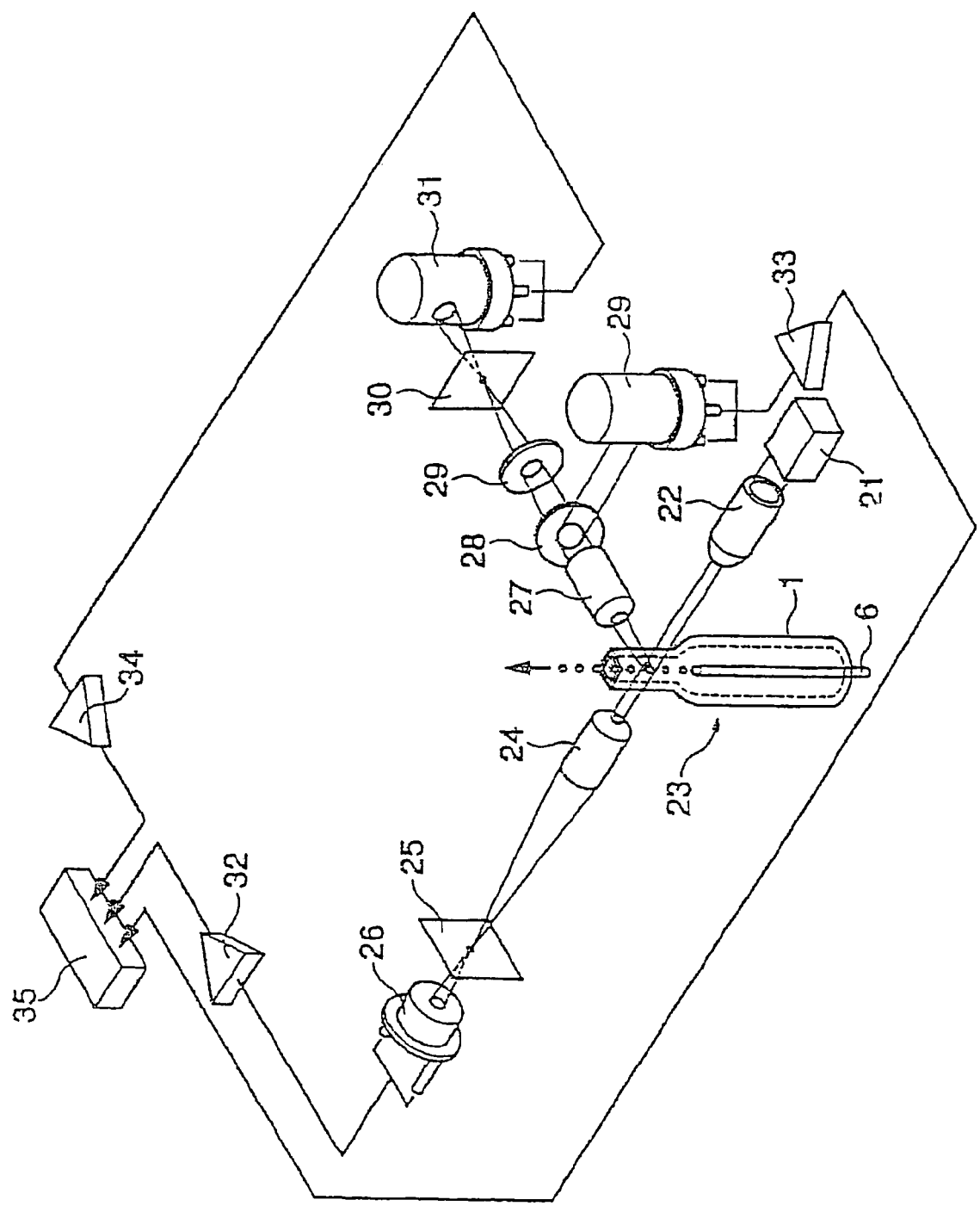
FIG. 18 is an oblique perspective figure showing an optical system of flow cytometer usable in the invention.

The above-mentioned bone marrow fluid was stained by May-Grünwald stain and observed visually under a microscope. The leukocytes were classified into lymphocytes, monocytes and granulocytes. In addition, using the above-mentioned blood, the DNA amount of the leukocytes was determined by a flow cytometer according to the standard method for measurement of the DNA amount. The results are shown in Table 3. Table 4 and FIG. 17 show the results obtained by the method of the invention conducted in the reaction time of 13 seconds and by the standard method for measurement of the DNA amount.

TABLE 3

|  | Present method (Reaction time: 7 sec) | Visual method |
|---|---|---|
| Lymphocyte (%) | 9.5 | 8 |
| Monocyte (%) | 16.4 | 18 |
| Granulocyte (%) | 6.8 | 9 |
| Myeloblast (%) | 2.3 | 1 |
| Granulocytic immature corpuscle (%) | 65.0 | 51 |
| Leukocyte with abnormal DNA amount (%) | 0 | 13 |
| Mature leukocyte: Leukocyte with abnormal DNA amount | 32.7:0 | 2.7:1 |
| Immature leukocyte: Leukocyte with abnormal DNA amount | 67.3:0 | 4:1 |
| Mature leukocyte: Immature leukocyte | 0.49:1 | 0.67:1 |

TABLE 4

|  | Present method (Reaction time: 13 sec) (%) | Standard method for measuring DNA amount (%) |
|---|---|---|
| Leukocyte with abnormal DNA amount | 11 | 13 |
| Normal leukocyte (in DNA amount) | 89 | 87 |

In conclusion, mature leukocytes and immature leukocytes can be measured precisely when the reaction time is 7 seconds, and leukocytes with abnormal DNA amount contained in immature leukocytes can be detected when the reaction time is 13 seconds.

As shown above, according to the invention it is possible to rapidly and simply measure leukocytes in which the DNA amount is abnormal.

The invention claimed is:

1. A method for classifying and counting leukocytes, which comprises:
   (1) a step of staining cells in a hematological sample by treatment with a hemolytic agent, with a fluorescent dye capable of differentiating in fluorescence intensity between mature leukocytes, leukocytes with abnormal DNA amount and immature leukocytes;
   (2) a step of introducing the sample containing the stained cells into a flow cytometer to measure first scattered light, second scattered light different from the first scattered light and fluorescence of the cells;
   (3) a step of obtaining scattered light peak intensities and scattered light widths of the cells based on the measured first scattered light, obtaining scattered light intensities of the respective cells based on the measured second scattered light, and obtaining fluorescence intensities of the cells based on the measured fluorescence light;
   (4) a step of classifying the cells into a first group and a second group based on the scattered light peak intensities and the scattered light widths, the first group including leukocytes and the second group including coincidence cells and platelet clumps;
   (5) a step of classifying the leukocytes included in the first group into mature leukocytes, leukocytes with abnormal DNA amount and immature leukocytes based on the scattered light intensities and the fluorescence intensities of the leukocytes included in the first group; and
   (6) a step of counting the classified mature leukocytes, the classified leukocytes with abnormal DNA amount and the classified immature leukocytes.

2. The method according to claim 1, which further comprises a step of calculating a ratio of mature leukocytes or immature leukocytes relative to leukocytes with abnormal DNA amount from a number of leukocytes with abnormal DNA amount and a number of mature leukocytes or immature leukocytes.

3. The method according to claim 1, which further comprises a step of calculating a ratio of immature leukocytes relative to mature leukocytes from a number of mature leukocytes and a number of immature leukocytes.

4. The method according to claim 1, wherein the fluorescent dye is selected from the group consisting of a compound represented by the formula (I):

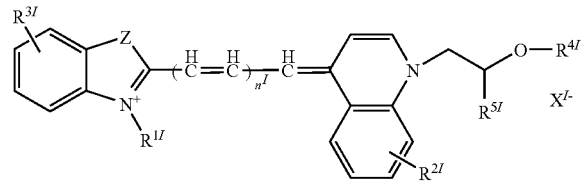

(I)

(wherein $R^{1I}$ is a hydrogen atom or a lower alkyl group; $R^{2I}$ and $R^{3I}$ each is a hydrogen atom, a lower alkyl group or a lower alkoxy group; $R^{4I}$ is a hydrogen atom, an acyl group or a lower alkyl group; $R^{5I}$ is a hydrogen atom or a lower alkyl group which may be substituted; Z is sulfur atom, oxygen atom, or carbon atom which is substituted by a lower alkyl group; $n^I$ is 1 or 2; and $X^{I-}$ is an anion), ethidium bromide, propidium iodide, ethidium-acridine heterodimer, ethidium azide, ethidium homodimer-1, ethidium homodimer-2, ethidium monoazide, TOTO-1, TO-PRO-1, TOTO-3, and TO-PRO-3.

5. The method according to claim 1, wherein the hemolytic agent comprises the following components:

(1) a polyoxyethylene nonionic surfactant;
(2) a solubilizing agent which damages to cell membrane of blood corpuscles and reduce their size;
(3) an amino acid; and
(4) a buffer having a pH range adjusted to 5.0-9.0 and osmotic pressure adjusted to 150-600 mOsm/kg.

6. The method according to claim 5, wherein the polyoxyethylene nonionic surfactant comprises a compound represented by the following formula (II):

$$R^{1II}-R^{2II}-(CH_2CH_2O)n_{II}-H \quad (II)$$

(wherein $R^{1II}$ represents a $C_{9-25}$ alkyl, alkenyl or alkynyl group; $R^{2II}$ represents —O—,

or —COO—; and $n_{II}$ is 10-40).

7. The method according to claim 5, wherein the solubilizing agent is a compound selected from the group consisting of a sarcosine derivative of the formula (III):

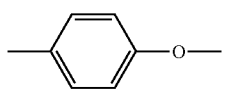

(wherein $R^{1III}$ is a $C_{10-22}$ alkyl group; and $n^{III}$ is 1-5) or salts thereof;

a cholic acid derivative of the formula (IV):

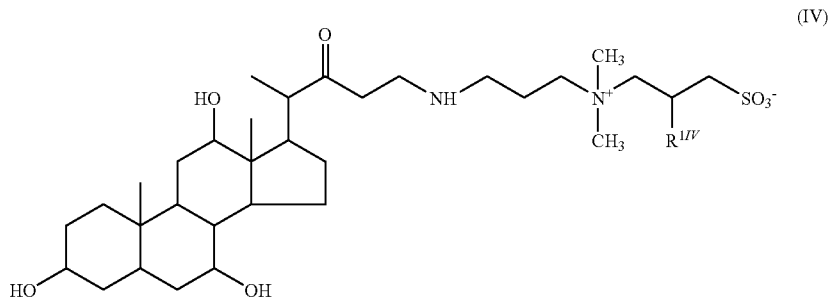

(wherein $R^{1IV}$ is a hydrogen atom or a hydroxy group); and
a methylglucanamide of the formula (V):

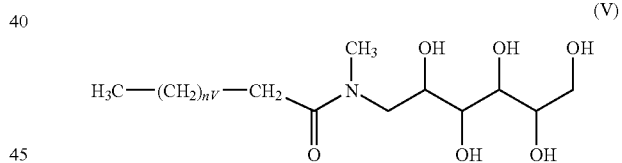

(wherein $n^V$ is 5-7).

8. The method according to claim 1, wherein scattered light to be measured is selected from forward low angle scattered light, forward high angle scattered light and side scattered light.

9. The method according to claim 1, wherein the classifying step (5) is performed so as to classify the classified mature leukocytes into at least three groups based on the scattered light intensities.

10. The method according to claim 1, wherein the classifying step (5) is performed so as to classify the classified immature leukocytes into at least two groups based on the scattered light intensities.

* * * * *